United States Patent [19]

Houseal et al.

[11] Patent Number: 5,627,029

[45] Date of Patent: May 6, 1997

[54] METHOD FOR OBTAINING INFORMATIVE CELLS

[75] Inventors: Timothy W. Houseal, Westborough; Karen Pavelka, Northbridge; Katherine W. Klinger, Sudbury; William R. Dackowski, Hopkinton, all of Mass.

[73] Assignee: Genzyme Corporation, Cambridge, Mass.

[21] Appl. No.: 243,647

[22] Filed: May 16, 1994

Related U.S. Application Data

[63] Continuation-in-part of Ser. No. 877,337, May 1, 1992, abandoned, which is a continuation-in-part of Ser. No. 695,267, May 3, 1991, abandoned.

[51] Int. Cl.$^6$ ............................ C12Q 1/68; H01L 21/20; C07H 21/02; C12N 15/00
[52] U.S. Cl. ........................ 435/6; 435/91.1; 435/810; 436/94; 536/23.1; 536/24.3; 536/24.31; 536/24.32; 935/77; 935/78
[58] Field of Search ..................... 435/6, 91.1, 810; 935/76–78; 536/23.1, 24.3, 24.31, 24.32; 436/94

[56] References Cited

U.S. PATENT DOCUMENTS

| | | |
|---|---|---|
| 3,910,819 | 10/1975 | Rembaum . |
| 4,499,183 | 2/1985 | Sujanski . |
| 4,707,448 | 11/1987 | Major . |
| 4,876,186 | 10/1989 | Frazier . |
| 5,153,117 | 10/1992 | Simons . |
| 5,177,002 | 1/1993 | Sinor .................................. 435/7.25 |
| 5,192,663 | 3/1993 | Yamamoto . |

OTHER PUBLICATIONS

Leonard, E.J. et la. (1990) "A Multiwell Cell Settling and Adherence Chamber for Morphology and Differential Counting" *BioTechniques*, 9(6):684–689.

Burns, J. et al. (1985) "Sensitive system for visualising biotinylated DNA probes hybridised in situ: rapid sex determination of intact cells" *J Clin Pathol* 38:1085–1092.

Pardue, M. (1985) "In Situ Hybridisation". *Nucleic Acid Hybridisation*, edited by Hames et al. pp. 179–202.

Rajendra, B.R. et al. (1980) "A New and Simple Technique for Chromosomal Preparations from Peripheral Blood Lymphocytes, Amniotic Cell Cultures, Skin Fibroblasts, Bone Marrow and Single Cell Clones when the Yields form Harvests are Low" *Human. Genet.*, 55:363–366.

Pardue, M. (1985) "In Situ Hybridization", *Nucleic Acid Hybridization*, Ed. Hames et al., pp. 179–202.

Rajendra et al., *Human. Genet.* 55:363–366 (1980).

*Primary Examiner*—Bradley L. Sisson

[57] ABSTRACT

The subject invention relates to a method for processing a liquid sample of biological material by: a) transferring a liquid sample containing both uncultured informative cells and non-informative cells onto a substrate wherein the surface tension of the liquid sample is sufficient to maintain the liquid sample beaded on the surface of the substrate; b) incubating the beaded liquid sample on the surface of the substrate for a period of time appropriate for the selective settling of the informative cells onto the surface of the substrate; and c) breaking the surface tension of the liquid portion of the sample wherein the liquid portion of the sample is removed along with the non-informative cells and wherein the informative cells remain on the surface of the substrate.

A kit for performing the method is also provided.

10 Claims, No Drawings

METHOD FOR OBTAINING INFORMATIVE CELLS

RELATED APPLICATIONS

This application is a continuation-in-part of U.S. Ser. No. 07/877,337, filed May 1, 1992, abandoned which is in turn a continuation-in-part of U.S. Ser. No. 07/695,267, filed May 3, 1991, abandoned the disclosures of which are incorporated herein by reference.

BACKGROUND OF THE INVENTION

In situ hybridization has been a major research tool for molecular geneticists to visualize specific DNA or RNA sequences present in cells. Originally performed in an isotopic format, non-isotopic techniques, such as fluorescence in situ hybridization (FISH), are rapidly becoming the method of choice, because they can be accomplished faster, multiple signals can be detected at one time and hybridization signals can be more precisely located.

In general, however, non-isotopic methods have suffered from a lack of sensitivity, especially if the samples to be analyzed include dead and/or degrading cells. Dead or degrading cells appear to be resistant to in situ hybridization, possibly because the nuclear DNA itself has begun to degrade and/or because the cells do not respond to the chemical reagents used in processing. The presence within a sample of cells which are resistant to in situ hybridization makes the analysis of any informative cells, which may also be present, difficult.

A method for preferentially isolating informative cells which produce clear hybridization signals in an in situ hybridization assay would be useful.

SUMMARY OF THE INVENTION

In one aspect, the subject invention relates to a method for processing a liquid sample of biological material by: a) transferring a liquid sample containing both uncultured informative cells and non-informative cells onto a substrate wherein the surface tension of the liquid sample is sufficient to maintain the liquid sample beaded on the surface of the substrate; b) incubating the beaded liquid sample on the surface of the substrate for a period of time appropriate for the settling of the informative cells onto the surface of the substrate; and c) breaking the surface tension of the liquid sample wherein the liquid portion of the sample is removed along with the non-informative cells.

In another aspect, the invention comprises the additional step of incubating the liquid sample with a protease inhibitor (e.g. phenylmethylsulfonylfluoride or benzamidine hydrochloride) and/or a salt of a short chain fatty acid (e.g. sodium butyrate, sodium propionate or sodium valerate) prior to or during its incubation on the substrate.

Once deposited, informative cells can be contacted with a fixative which preserves and retains nucleic acids within the cells for genetic analysis.

The methods of the subject invention result in clean preparations of informative cells having large and flat nuclei. In situ analysis of such preparations is easier to perform and results are more interpretable. Therefore, using the disclosed methods, diagnostic evaluations based on in situ analysis can be made with increased confidence.

DETAILED DESCRIPTION OF THE INVENTION

One embodiment of the subject invention is based upon the surprising finding that informative cells can be separated from non-informative cells by a settling procedure. Informative cells are cells which provide an interpretable hybridization signal in an in situ hybridization assay. In contrast, non-informative cells, do not provide an interpretable hybridization signal. Another embodiment of the invention is based on the finding that certain agents can be added to produce clean preparations of informative cells having large and flat nuclei which can be more readily analyzed by in situ hybridization analysis.

The term "cellular material" refers to any target of an assay such as nucleic acids or proteins.

Cells that are the subject of analysis using the method of the present invention, generally come in the form of uncultured cells in clinical samples. Samples, clinical samples in particular, contain a mixture of informative cells (i.e., cells that provide an interpretable hybridization signal) and non-informative cells (i.e., cells that do not provide an interpretable hybridization signal). Examples of such samples include fetal cells (e.g. obtained from amniotic fluid, maternal blood, cord blood, chorionic villus tissue or cervical secretions), lymphocytes (e.g. obtained from blood), embryonic cells (e.g. obtained from a biopsied embryo), and cancer cells (e.g. obtained from a tumor). Cells from a dry sample must be converted to a liquid format, for example, placing the cells in a buffered solution. In some cases, it may be necessary to concentrate the cells in a liquid sample prior to placing them on the substrate to increase the number of cells in the microscopic field analyzed. The concentration of cells can be done by various methods known by those of skill in the art (e.g., by centrifugation). If centrifuged, the cell pellet can then be resuspended in phosphate buffered saline (PBS) or any other inert buffered solution.

After concentrating the cells, if required, a portion of the liquid sample containing suspended cells is deposited onto a substrate. The amount of sample (i.e., volume of liquid) placed on the substrate must be an amount sufficient to bead up on the surface, but not an amount more than would cause the liquid to run off the edges of the substrate's surface. For example, for some etched-ringed glass slides, an amount of water greater than 250 µl will break the surface tension of the water and the water will spill over the edges of the substrate.

Once beaded up on the substrate, the cells, both informative and non-informative cells which are suspended in the liquid, are allowed to incubate for a period of time long enough for a sufficient number of informative cells to settle, but not so long that non-informative cells would settle, i.e., the non-informative cells remain suspended in the liquid. The appropriate incubation period can range from about 1 to about 60 minutes with from about 15 to about 30 minutes being optimal. There does not appear to be a strong dependence on temperature for preferential cell settling. For example, experiments have been conducted at room temperature and at 37 degrees C. with no clear difference in the quality of the preparation.

Once the informative cells are allowed to settle, the surface tension of the liquid, which contains the non-informative cells suspended within it, is broken and a substantial amount of the liquid is allowed to spill over the edges of the substrate taking the non-informative cells with it. The surface tension can be broken by tilting the surface of the substrate allowing the liquid to pour over an edge. It should be noted that we have shown that a dilute fixative (e.g., dilute Carnoy's fixative) can be added to the beaded liquid sample prior to breaking the surface tension to remove the non-informative cells and the liquid.

Certain agents can be added to the buffered solution containing the subject cells either prior to or during their incubation on the substrate which enhance the preferential deposition of informative cells. For example, phenylmethylsulfonylfluoride (PMSF) in a concentration range of 0.01 to 1.0 mM has been found to improve settling efficiency. Other protease inhibitors such as benzamidine hydrochloride (BZA) may also be useful for settling informative cells in preference to non-informative cells. In addition, agents which have the effect of enlarging the nuclei and/or making them flat or in any way make the nuclei more available for hybridization may be added to the buffered solution containing the cells prior to or during the incubation on the substrate. For example, a salt of a short chain fatty acid in a concentration range of 1 to 100 mM (such as sodium butyrate, sodium propionate and sodium valerate) when added to the preparation appears to free nuclei from cells, thereby rendering the nuclei more available for in situ hybridization. Also, incubation of informative cells in a hypotonic solution has been found to induce cells to swell, thereby spreading the cellular constituents and increasing the probability that the nucleus will be well-exposed in the final preparation.

While the cells can be deposited and incubated on such substrates as glass, plastic or nitrocellulose, a glass microscope slide is the preferred substrate, because it can be readily manipulated and viewed under a microscope. The substrate can be pretreated with a "cell adherent" which improves the likelihood that a cell settling onto the surface remains attached during subsequent manipulations. A preferred cell adherent is 3-Aminopropyltriethoxysilane. Treatment with this adherent results in "silanized" substrates. Other adherents useful in the subject invention include: poly-L lysine and mussel adhesin. Pretreatment of solid substrates can be accomplished using any method that ensures that the cell adherent is deposited (e.g. submersion, transferring using a dropper, etc.). Pretreated solid substrates can be stored in a dust free environment at room temperature.

Once the informative cells are allowed to preferentially settle, they can then be processed through a fixation protocol to preserve the nuclei or chromosomes in a morphologically stable state so that nucleic acids (i.e., cellular material) are retained through the rigorous conditions present during in situ hybridization. Appropriate fixatives are well-known in the art and include, for example, 4% paraformaldehyde or glutaraldehyde in phosphate buffered solution (PBS) containing 5 mM $MgCl_2$, a fixative containing 3 parts ethanol and 1 part acetic acid, Carnoy's fixative, 1% osmium tetraoxide, Bouin's fixative, and Zenker's fixative. In order to prevent loss of cellular material from a support, the fixative can either be applied directly to deposited (settled) material, in a small amount or a larger volume of a diluted solution can be applied. The supports can then be dried in preparation for in situ analysis.

A kit comprising the solutions of the subject invention which can be used for preparing cellular material can be produced. It can include, for example, a container for holding the required components, supports on which cellular material can be deposited, solutions for fixing informative cells, a protease inhibitor (e.g. PMSF or BZA) and a short chain fatty acid (e.g. sodium butyrate, sodium propionate or sodium valerate). A kit may also optionally include probes and solutions to stain probes.

The present invention will now be illustrated by the following examples, which are not intended to be limiting in any way.

EXAMPLE 1

Method for Preparing a Cell Sample for In Situ Analysis

Solutions

PBS:

32 g NaCl, 0.8 g KCl and 8.68 g $NaH_2PO_4 \cdot 7H_2O$. Make up to 4 liters with distilled $H_2O$, pH to 7.5.

Carnoy's Fixative:

75 ml methanol 25 ml glacial acetic acid 0.075M KCl:

Dissolve 5.59 g KCl in 1 liter distilled $H_2O$. Filter sterilize using 0.2 micron filter flask.

30% Fix in 0.075M KCl:

3 ml Carnoy's Fixative 7 ml KCl

Preparation of Aminoalkylsilane Coated Slides

A 2% solution of 3-Aminopropyltriethoxysilane was prepared by mixing 5 mls of 3-Aminopropyltriethoxysilane with 250 ml acetone. Clean glass microscope slides were placed in a slide rack and submerged for 2 minutes in the 2% solution described above. Following submersion, slides were removed from solution and rinsed in two changes of distilled water. Slides were then drained and allowed to air dry. Prepared slides were stored in a dust-free box at room temperature.

Sample Preparation for Settling Onto Slides

An amniotic fluid sample was spun in a centrifuge tube at 2100 RPM (1029 G) for 7 minutes at room temperature. The supernatant was then removed by aspiration. The remaining pellet was resuspended in 50 µl of PBS per 1 ml of original fluid volume. 25 µl of resuspended pellet in PBS was then placed on a silanized glass microscope slide (prepared as described above). If a substantial amount of blood was present in the amniotic fluid, 1 drop of 30% 3:1 methanol:glacial acetic acid fixative (Carnoy's fixative) in 70% 0,075M KCl was added.

Slides were placed horizontally in a humid chamber at a temperature of 37 degrees C. for 15 minutes. This incubation period allows informative cells to settle onto the surface of the silanized slide surface undisturbed. Dead cells, or other cells having damaged membranes, remain floating in the buffer.

Preparation of Cells Settled Onto Slides for In Situ Analysis

After 15 minutes, 50 µl of 0.075M KCl hypotonic solution (prewarmed to 37 degrees C.) was gently added to the buffered solution containing the resuspended cell pellet followed by an additional 15 minutes incubation in the heated humid chamber. Hypotonic solution causes viable cells to swell, making it easier to remove cytoplasm and cell membrane in subsequent steps.

After 15 minutes of incubation in KCl at 37 degrees C., the fluid was gently tipped from each slide (to the side, not lengthwise). The slides were not allowed to dry at this step. After each slide was tipped, it was placed flat on a paper towel and 100 µl of 30% Carnoy's fixative in 0.075M KCl was gently added. The slides were left undisturbed in this condition for a period of 5 minutes. The 30% fix/KCl solution ruptures the swollen cell membranes and conditions the cells to the fix.

After a 5 minute incubation period, fluid was gently tipped from each slide. The slides were not allowed to dry out. 5–6 drops of fresh undiluted Carnoy's fixative were immediately dropped onto the region of the slide containing the cells. The slides were incubated for approximately 5 minutes then transferred to a 60 degree C. slide warmer and allowed to dry. This fixative treatment ruptures any remaining membranes and rinses away residual debris while fixing the nuclei to the slide.

Once dried, slides containing fixed cells were processed through an ethanol series prior to hybridization. In coplin jars, the slides were contacted sequentially with 70%, 80%, 90% and 100% ethanol for 1 minute in each dilution. The slides were then allowed to dry at room temperature.

EXAMPLE 2

Method for Preparing a Cell Sample for In Situ Analysis Which Includes the Addition of Sodium Butyrate and PMSF Amniotic fluid samples were prepared as described in Example 1, but with the following modifications:

1. Sodium butyrate was added to a concentration of 10 mM and samples were incubated at room temperature for up to 2 hrs. Subsequent experiments have shown that this incubation may be as little as 5 minutes.
2. 20 mM sodium butyrate and 0.5 mM phenylmethylsulfonylfluoride were added to the buffer used to resuspend the pellet generated by centrifugation.

In Situ Hybridization Analysis

Fixed slides were placed on a 60° C. slide warmer for 1–2 hours before hybridization. A nucleic acid probe specific to a sequence on chromosome 13, 18, 21, X or Y about 35 kbs in length was labeled with biotin by nick translation. Each hybridization reaction contained 5–10 ng/µL of the biotin labeled probe, and 100 ng/µL of human Cot-1 DNA, 900 ng/µl of salmon DNA in a cocktail of 50% deionized formamide, 6XSSC, and 10% Dextran Sulphate. A 5–10 µL aliquot of hybridization cocktail was applied to each site, coverslipped, and sealed with rubber cement. Probe and target were simultaneously denatured for 7–10 min at 80° C. After overnight hybridization at 37° C. slides were processed in the following manner: Slides were washed for 3×5 min in 50% formamide/2XSSC at 42° C. 1×5 min in 2XSSC at room temperature, and 3×5 min in 0.1XSSC at 60° C. Non-specific binding sites were blocked by incubation at 37° C. in 3% BSA/4XSSC for 5 min. Hybridized probe was detected with a solution containing 2.0 ng/µL of Cy3 conjugated to streptavidin in 1% BSA, 1% Tween 20 (polyoxyethylene-sorbitan) monolaurate and 4XSSC; preparations were incubated in this solution for 20 min at 37° C. Following detection, slides were washed for 3×5 min in 4XSSC with 0.1% Tween 20 at 42° C., then washed in 2XSSC for at least 5 min at room temperature. Preparations were counterstained with 4',6-diamidino-2-phenylindole (DAPI) and mounted in 2.33% DABCO (Sigma, #D2522, St. Louis, Mo.) in 100 mM Tris (pH 8.0) and 90% (vol:vol) glycerol. Post hybridization washing and detection are essentially as described in Klinger et. al. *Am. J. Hum. Genet.* 51: 55–65 (1992).

Results

Many more informative nuclei were recovered than when using the protocol described in Example 1 in a side-by-side comparison with the same amniotic fluid sample. Anywhere from 3–25 times more nuclei were recovered and, of those, 88% (on average) were able to hybridize. There was a greater absolute number of nuclei and more of these were informative. Therefore, less sample is required for performing an analysis. Most hybridization signals were in the same focal plane or could be seen from one focal plane, suggesting that these nuclei were also flatter than those recovered using the protocol in Example 1.

EXAMPLE 3

In Situ Analysis of Cells From Embryos

Embryo Retrieval and Cell Preparation for FISH

Embryos at the 8–16 cell stage were flushed from the uteri/oviducts of pregnant females with Hanks Buffered Salt Solution (HBSS) and BSA. The zona pellucida was removed from the morula by a brief exposure to prewarmed acidic Tyrodes solution (Manipulating the Mouse Embryo: A Laboratory Manual ed. Hogan, Constantini and Lacy (Cold Spring Harbor Laboratory, 1986). The morula stage embryos were then incubated in calcium-free CZB medium with 5 mg/ml BSA for 20 min. at 37° C. in 5% $CO_2$ in air to decompact the embryos. The embryos were then disaggregated to single cells using a polished micropipet. The dissociated morula cells were then processed for FISH.

The cells were transferred into 10 µl of TB buffer (T Buffer: 1 mM Tris; 25 mM KCl; 0.9 mM $CaCl_2$; and 0.9 mM $MgCl_2$ at pH 7.6; TB Buffer: T Buffer plus 20 mM sodium butyrate or TB/PMSF buffer: TB buffer containing 1/100 dilution of 50 mM PMSF in isopropanol) on a siliconized Teflon® masked glass slide (Cel-line Assoc, Newfield, N.J.) for 15 min. Then 20 µl of 0.3% hypotonic sodium chloride was added to the drop for 15 min. Fixation was achieved by adding 5 µl of Carnoy's (3:1 methanol:acetic acid solution) for 10 min, followed by the addition of 40–60 µl of Carnoy's. The samples were allowed to air dry or in some cases, the excess fixative was removed by tipping the slide briefly on its side, then allowed to dry slowly in a humid chamber.

In Situ Hybridization Analysis

Fixed slides were placed on a 60° C. slide warmer for 1–2 hours before hybridization. A nucleic acid probe for an endogenous mouse sequence about 35 kbs in length was labeled with biotin by nick translation. Each hybridization reaction contained 5–10 ng/µL of the biotin labeled probe, 100 ng/µL of mouse Cot-1 DNA and 900 ng/µl of salmon DNA in a cocktail of 50% deionized formamide, 6XSSC, and 10% Dextran Sulphate. A 5–10 µL aliquot of hybridization cocktail was applied to each site, coverslipped, and sealed with rubber cement. Probe and target were simultaneously denatured for 7–10 min at 80° C. After overnight hybridization at 37° C., slides were processed in the following manner: Slides were washed for 3×5 min in 50% formamide/2XSSC at 42° C., 1×5 min in 2XSSC at room temperature, and 3×5 min in 0.1XSSC at 60° C. Non-specific binding sites were blocked by incubation at 37° C. in 3% BSA/4XSSC for 5 min. Hybridized probe was detected with a solution containing 2.0 ng/µL of Cy3 conjugated to streptavidin in 1% BSA, 0.1% Tween 20 and 4XSSC; preparations were incubated in this solution for 20 min at 37° C. Following detection, slides were washed for 3×5 min in 4XSSC with 0.1% Tween 20 at 42° C., then washed in 2XSSC for at least 5 min at room temperature. Preparations were counterstained with 4',6-diamidino-2-phenylindole (DAPI) and mounted in 2.33% DABCO (Sigma, #D2522) in 100 mM Tris (8.0) and 90% (vol:vol) glycerol. Post hybridization washing and detection are essentially as described in *Klinger et. al.* (1992).

Results

The results are summarized in Table 1. A total of 209 morula cells were obtained from three independent experiments; 166 of these (79.5%) were recovered after processing in the manner described. Hybridization signal was detected in all (100%) of the recovered cells. These results demonstrate good recovery of embryonic cells (nearly 80%) and 100% hybridization efficiency. These results suggest that these procedures can be applied to the analysis of biopsied cells from preimplantation embryos.

TABLE 1

| Example | Cell Recovery (%) | Hybridization Signal |
|---------|-------------------|----------------------|
| 1 | 55 of 78 (71%) | 55 |
| 2 | 57 of 77 (74%) | 57 |
| 3 | 54 of 54 (100%) | 54 |
| TOTAL | 166 of 209 (79.5%) | 166 |

Equivalents

Those skilled in the art will know, or be able to ascertain using no more than routine experimentation, many equivalents to the specific embodiments of the invention described herein. These and all other equivalents are intended to be encompassed by the following claims.

We claim:

1. A method for processing a liquid sample of uncultured cells for in situ hybridization analysis, wherein the sample cells that are informative are separated from sample cells that are non-informative, comprising the steps of:

a) transferring a liquid sample containing both uncultured informative cells and non-informative cells onto a solid substrate wherein the surface tension of the liquid sample is sufficient to maintain the liquid sample beaded on the surface of the solid substrate;

b) incubating the beaded liquid sample on the surface substrate for a period of time in the range of about 15 minutes to about 30 minutes for the selective settling of informative cells onto the surface of the solid substrate; and c) breaking the surface tension of the liquid sample wherein the liquid portion of the sample is removed along with the non-informative cells and wherein the informative cells remain on the surface of the solid substrate.

2. A method according to claim 1, wherein the solid substrate is pretreated with a cell adherent.

3. A method according to claim 1, wherein the sample is selected from the group consisting of amniotic fluid, chorionic villus tissue, maternal cervical secretions, cord blood, adult blood and cells biopsied from embryos.

4. A method according to claim 1, wherein the method further comprises contacting the informative cells with a fixative prior to or after step c).

5. A method for processing a liquid sample of uncultured cells for in situ hybridization analysis, wherein the sample cells that are informative are separated from the sample cells that are non-informative, comprising the steps of:

a) incubating liquid sample with phenylmethylsulfonylfluoride (PMSF);

b) transferring the liquid sample of step a) containing both uncultured informative cells and non-informative cells onto a solid substrate wherein the surface tension of the liquid sample is sufficient to maintain the liquid sample beaded on the surface of the solid substrate;

c) incubating the beaded liquid sample on the surface of the solid substrate for a period of time in the range of about 15 minutes to about 30 minutes for the selective settling of informative cells onto the surface of the solid substrate; and d) breaking the surface tension of the liquid sample wherein the liquid portion of he sample is removed along with the non-informative cells and wherein the informative cells remain on the surface of the solid substrate.

6. A method according to claim 5, wherein the solid substrate is pretreated with a cell adherent.

7. A method according to claim 5, wherein said method renders nuclei more available for in situ hybridization by the addition of a salt of a short chain fatty acid which is selected from the group consisting of sodium butyrate, sodium propionate and sodium valerate.

8. A method according to claim 5, wherein the sample is selected from the group consisting of amniotic fluid, chorionic villus tissue, maternal cervical secretions, cord blood, adult blood and cells biopsied from embryos.

9. A method according to claim 5, wherein the method further comprises contacting the informative cells with a fixative prior to or after step d).

10. A kit for preparing cells for in situ hybridization analysis, comprising:

a) a container for holding the components;

b) a solid substrate;

c) a protease inhibitor comprising phenylmethylsulfonylfluoride (PMSF)

d) a short chain fatty acid selected from the group consisting of sodium butyrate, sodium propionate and sodium valerate;

e) a fixative; and f) a nucleic acid probe (s).

* * * * *